United States Patent [19]

Tauber

[11] 4,070,660
[45] Jan. 24, 1978

[54] WEAR PARTICLE DETECTOR

[76] Inventor: Thomas E. Tauber, 24 E. Glenolden Ave., Glenolden, Pa. 19036

[21] Appl. No.: 659,948

[22] Filed: Feb. 20, 1976

[51] Int. Cl.² .............................................. G08B 21/00
[52] U.S. Cl. ................................. 340/236; 200/61.09; 335/305; 340/270
[58] Field of Search ................... 340/236, 239 R, 270; 324/41, 55; 200/61.09; 335/302, 305

[56] References Cited

U.S. PATENT DOCUMENTS

| 2,429,920 | 10/1947 | Bourne, Jr. | 340/270 |
| 2,450,630 | 10/1948 | Bourne, Jr. | 340/270 X |
| 3,193,815 | 7/1965 | Prestel | 340/236 |
| 3,432,750 | 3/1969 | Botstiber | 340/270 X |
| 3,622,882 | 11/1971 | Gardner | 324/55 X |

Primary Examiner—John W. Caldwell, Sr.
Assistant Examiner—Daniel Myer
Attorney, Agent, or Firm—Robert S. Lipton

[57] ABSTRACT

A wear particle detector for use with hydraulic systems, capable of collecting wear particles formerly suspended in the hydraulic fluid and of discriminating between larger and smaller particles by indicating the former, but destroying the latter automatically without causing detection, whereby both device functions are connected to and energized by the same single electric power supply and indicating circuit.

11 Claims, 6 Drawing Figures

WEAR PARTICLE DETECTOR

BACKGROUND

Conventional wear particle detectors capture metal particles which are present in the fluid of a hydraulic system, or more particularly, in the lubricant of an engine or transmission. These metal particles are induced to bridge a gap between two electrodes of such a device and thereby complete an electric circuit. Upon closing of the electric gap by the metal particles, an external warning signal is activated.

In systems whose moving components are primarily of steel, the effectiveness of the device is increased by a magnetic field between or in the direct proximity of the electrodes. In some systems, more than one pair of electrodes is used in order to increase the probability of metal particles closing the electric circuit. These ancillary provisions have no direct influence on the principle of this invention.

It is obvious that the same effect may result from the bridging of the electric gap by one metal particle of substantial size or by several metal particles of small size(s) in contact with the electrodes and with each other.

In particular, during normal operation of the engine, transmission or other hydraulic or fluid system, very fine particles are generated by the normal wear of power transmitting surfaces. This condition is particularly prevalent when the equipment is new and the power transmitting surfaces of gears, bearings and other components are in the initial wear process, commonly referred to as the run-in period. An accumulation of these very small particles, usually termed "wear fuzz," can cause an activation of the warning signal, even though no hazard exists, amounting to a so-called nuisance indication. If such devices are employed in engines, transmissions, gear boxes and auxiliary drives of, especially, aircraft, costly and unwarranted precautionary measures may result.

It would, therefore, be desirable to limit the activation of the warning signal to those cases where a metal particle of a larger size, such as produced by initial failure of a metal surface, bridges the gap between the electrodes of the device.

SUMMARY OF INVENTION

The subject of this invention is a wear particle detector capable of attracting and indicating the presence of larger-sized particles causing an alarm indication through an appropriate, however, straightforward electric circuit but also devised to destroy smaller, wear-fuzz type particles automatically and recurrently through the utilization of the very same electric circuit, thereby precluding additional electric circuit installations, signal observations and commands, as well as nuisance indications together with their adverse flight-operational consequences.

Devices are known which destroy wear fuzz by utilizing a large, more or less constant, electric current from a secondary power source and in which the presence of a particle lodged across the electric contact gap is indicated through a first electric circuit incorporating a warning device. Following activation of the warning device, an operator causes said wear fuzz to be destroyed by routing, for a certain period of time, said large electric current of essentially constant magnitude through the electric contact gap. Said secondary power source may consist of a low resistance branch of the power supply system or the indicating circuit. This method has several considerable disadvantages. Firstly, the large current required to destroy wear fuzz particles of typical cross section causes a heavy power drain on the electric system of, for example, an aircraft. Secondly, specialized circuit protection devices are required which limit the magnitude of the electric current so that safe operating limits may not be exceeded. These devices are bulky and dissipate undesirable amounts of heat. Thirdly, and most importantly, a given wear particle may or may not be destroyed by a current of predetermined and essentially constant magnitude, depending upon the duration of its application and upon the rate at which the heat generated by said current is dissipated into the environment. This introduces a substantial element of uncertainty into the operation of such devices and results in low operator confidence in the outcome of such an operating cycle. For these reasons, devices of this kind are not at present popular in industry.

In contrast to those devices of an essentially resistive type requiring constant monitoring and manually operated, secondary electric circuits, the device according to this invention accomplishes said war fuzz destruction automatically by means of at least one capacitor arranged within the basic electric circuit and, additionally, by providing means for the retention of wear particles to facilitate their detection and selective destruction, respectively.

Said capacitor is and remains charged automatically until wear fuzz becomes lodged across the gap between the electrodes of the device, whereupon the capacitor discharges its stored electric energy through said wear fuzz, causing its destruction without burden to the power supply system, the opening of said gap and the automatic and immediate recharging of said capacitor without the occurrence of an, in this case, nuisance indication.

If, on the other hand, a failure particle, characterized by a larger cross section, becomes lodged in said gap, said capacitor discharges in a similar manner but without destroying said particle, whereupon a warning light is activated automatically and the capacitor remains discharged.

Since the destruction of said wear fuzz upon the discharge of said capacitor requires only an extremely short period of time, the rate of heat dissipation during this process, all other environmental conditions being equal, does not affect the outcome of the operating cycle. The device is, therefore, capable of unequivocally distinguishing between smaller wear fuzz particles and larger failure particles and of the selective suppression of nuisance indications.

Further advantages of the subject invention — per se — and over prior art will become apparent from the following description and the accompanying drawing.

In the drawing, forming a part of this application,

FIG. 1 presents a diagram of the electric circuit required for the operation of the wear particle detector, FIG. 2 shows, in front elevation and cross section in the plane II—II, a possible assembly of a wear particle detector equipped with the required component parts and internal wiring, FIG. 3 portrays, in front elevation, an outside view of the assembly of said wear particle detector, FIG. 4 indicates an electric circuit diagram of a wear particle detector having differentiating and selective response features, FIG. 5 depicts an electric circuit diagram of a wear particle detector providing a warning for taking remedial action, and FIG. 6 illustrates, in front elevation and cross section in the plane II—II, a modified detail of FIG. 2.

DESCRIPTION OF THE PREFERRED EMBODIMENT

Figure 1:
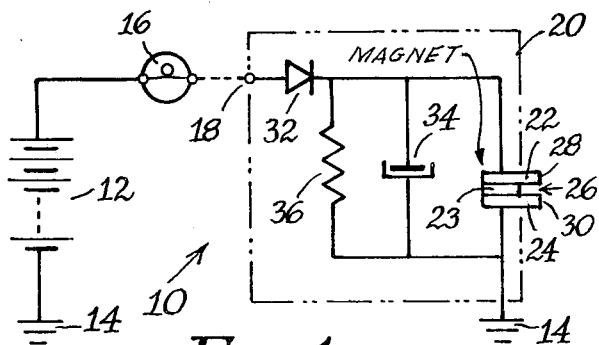

Referring now to the drawing, wherein like reference characters designate like or corresponding parts, and, particularly, to FIG. 1, constituting a symbolic diagram of the electric circuit 10; the connecting wires shown in solid lines are those, for example, built into the subject wear particle detector 20, whereas those in dotted lines apply to external electric wiring and components with which said device 20 is operationally connected. A power source 12, such as a battery, has a return terminal 14 at, say, its negative pole, and its positive pole is connected to one terminal of an electric bulb 16. The other terminal of said bulb 16 is connected to the terminal 18 of said device 20.

The wear particle detector 20 contains the two electrodes 22 and 24, which may also be the pole pieces of a magnetic circuit, in which case they are permanently magnetized in opposite polarity with respect to each other and electrically insulated from each other through the insulator 23. Said insulator 23 may consist of a permanent magnet of an electrically nonconductive material. Said electrodes 22 and 24 are arranged so as to form an operational gap 26 of a specific, predetermined dimension between them. It should be noted that the faces 28 and 30 of the electrodes 22 and 24 will be exposed to the hydraulic fluid whereas the other parts of the wear particle detector will be mounted within an enclosure as indicated, schematically, through a phantom line, in FIG. 1.

The electrode 24 is connected to the return, preferably by means of the enclosure of the wear particle detector. The electrode 22 is further connected to the negative pole of the diode 32, whereas its positive pole is wired to the terminal 18 of the device 20. A capacitor 34 is connected across the electrodes 22 and 24 and their gap 26.

On the basis of the foregoing, the operation of said wear particle detector is as follows: As soon as the terminal 18 is connected to the power source 12, through the bulb 16, and system voltage is applied to the electrodes 22 and 24, the capacitor 34 becomes charged. If a particle becomes lodged in the gap 26 formed by said electrodes 22 and 24 and is securely arrested by the magnetic field, so as to bridge said gap and thereby closing the electric circuit, the capacitor 34 discharges through said particle bridging said gap 26. If said particle has a cross-sectional area large enough to prevent it from becoming melted and disintegrated, respectively, through the discharge current impulse of said capacitor 34, it will cause the bulb 16 to light which, in turn, will indicate the presence of a substantial particle and a failure condition. If, however, one or more particles of wear fuzz dimensions have been attracted and eventually bridge said gap 26, they will become destroyed under the effects of the capacitor discharge impulse current which, in turn, opens the circuit without causing a lighting of said bulb 16, thusly allowing for the immediate recharging of said capacitor 34 and its recurrent operation. The diode 32 is to block the aforementioned discharge current impulse effects from reflecting to other wear particle detectors of this kind installed elsewhere in the aircraft. The bleeder resistor 36 is provided so as to slowly discharge said capacitor 34 when the power source is turned off. This is of particular importance when the wear particle detector 20 is removed from the aircraft for inspection and maintenance to prevent possible damage to inspection instruments.

Figure 2:
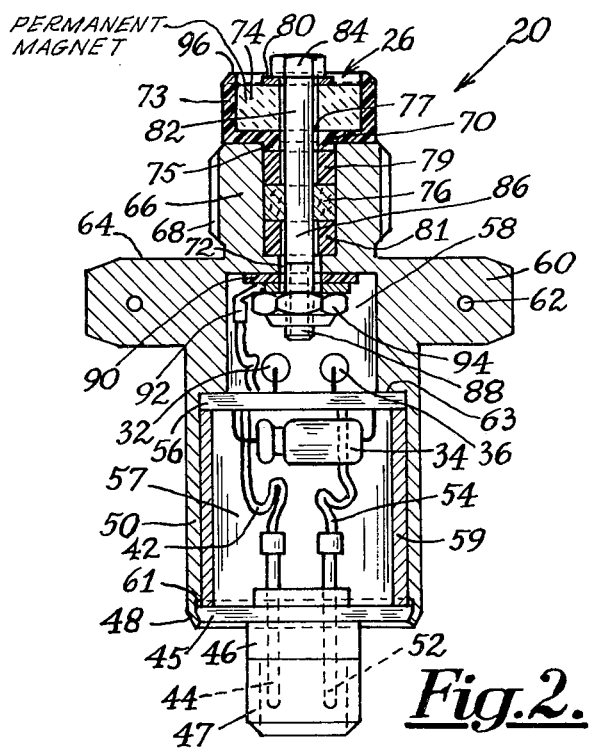

A possible practical configuration of a said wear particle detector 20, as shown in FIG. 2, indicates a typical construction enumerated, substantially, in the sequence of the foregoing description.

The terminal 18 of the wear particle detector 20 is, in this case, a pin contact 44 of a conventional connector receptacle 46 having the external thread 47 formed thereon so as to accommodate a mating plug (not shown). The receptacle 46 is mounted concentrically with the axis of the wear particle detector 20 on a face plate 45.

A second pin contact 52 is internally connected to the substantially cylindrical enclosure 50 through the wire 54, thusly "grounding" said pin contact 52 through its return connection and the electrically conductive installation of said wear particle detector 20 to the respective equipment (not shown). It should be noted that this pin contact 52 and its connecting wire may not be required if adequate electrical continuity exists between said enclosure 50 and the negative return pole 14 of said power source 12.

A circuit board 56 is positioned inside said enclosure 50, seated against the annular shoulder 63, dividing the inside of said enclosure 50 into an upper port 58 and a lower port 57, each concentric with the axis of said enclosure 50. A spacer 59, having the shape of a hollow, thin-walled cylinder is positioned inside of and contiguous with the lateral inside surface of said lower port 57. The upper, annular face of said spacer 59 abuts with the lower surface of said circuit board 56, whereas the lower annular face of said spacer abuts with the upper surface of the face plate 45.

The bottom wall portion 48 is formed at the lower end of said enclosure 50, whereby the inside diameter of said bottom wall portion is larger than the inside diameter of said lower port 57, resulting in an annular shoulder 61.

Upon completion of the assembly of said wear particle detector 20, the bottom wall portion 48 is then turned over the lateral side of said face plate 45, leaving a clearance space between the upper surface of face plate 45 and said annular shoulder 61 in accordance with good manufacturing practice.

A capacitor 34 is mounted on, say, the bottom face of said circuit board 56, whereas said diode 32 and said bleeder resistor 36 are mounted on the top side of said circuit board 56. The line side of the foregoing components is connected to said pin contact 44 through the wire 42, as shown in the schematic FIG. 1. It should be emphasized that either and all of these elements, namely, said capacitor, resistor and diode, may be located, alternatively, exteriorly and remotely with respect to said device enclosure 50.

A, for example, hexagon shaped flange 60, having safety wiring provisions 62, is formed at the outside of said enclosure 50. The annular face 64 of said flange 60 is horizontal with respect to this view and, together with a conventional gasket or an O-ring (not shown), provides a dependable seal with the mating, annular surface of a boss formed on the case of a piece of equipment (not shown). An extension 66, being substantially an offset hollow cylinder and having an external thread 68 formed thereon, is arranged on top of said flange with respect to this view, providing a cylindrical hole 72 and a cylindrical, upwardly open port 70 in its interior concentric with the axis of said wear particle detector 20.

A cylindrical, substantially cup-shaped, upwardly open receptacle 73 of ferrous material having a cylindrical offset extension 75 at its bottom and a cylindrical hole 77 concentric with the axis of said device formed through its bottom and said extension 75, whereby the diameter of said offset extension 75 is of a dimension to allow for its insertion into said port 70.

Figure 6:
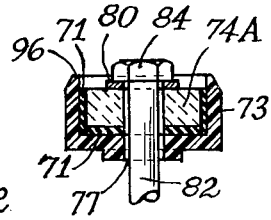

A permanent magnet 74 of the ceramic, electrically nonconductive type and of annular shape is lodged within said cup-shaped receptacle 73. It should be noted that in place of said ceramic, electrically nonconductive permanent magnet 74, a permanent magnet 74A of an electrically conductive material can be used. In this case, as illustrated in FIG. 6, a sheath 71 of an electrically nonconductive material is mounted between the lateral side of said ferrous magnet 74A and the lateral inside of said receptacle 73, and between the bottom face of said magnet 74A and the bottom face of said receptacle 73.

A first annular, electrically nonconductive spacer 79, an annular seal 76 and a second annular, electrically nonconductive spacer 81 are provided underneath said receptacle 73 and within said first port 70.

A washer 80 of an electrically and magnetically conductive material constituting, simultaneously, a first magnetic pole and a first electrode 22, is placed on top of and concentrically with said annular, permanent magnet 74 or 74A, respectively. A screw bolt 82 of electrically conductive material having, for example, a hexagon shaped head 84, a shank 86, having a threaded end portion 88, whereby said shank passes through said washer 80, said magnet 74 or 74A, respectively, said receptacle extension 75, said spacer 79, said seal 76, said spacer 81 and with its threaded end 88 beyond the foregoing parts and through the hole 72 into said upper port 58. A washer 90 of any suitable insulating material is provided concentrically with the axis of said enclosure 50 so as to seat with its upper annular surface on the annular surface of said upper port 58.

A wire terminal 92 is arranged below said washer 90, connecting said washer 80, being the electrode 22, with the other circuit components as illustrated in FIGS. 1 and 2, respectively. A, for example, hexagon nut 94 is mounted on the threaded shaft portion 88, which, when tightened, accomplishes the assembly of said electrically and magnetically conductive washer 80, said permanent annular magnet 74 or 74A, respectively, said cup-shaped receptacle 73, said first annular spacer 79, said annular seal 76, said second annular spacer 81, said electrically nonconductive washer 90 and said wire terminal 92, together with its wire, within said enclosure 50.

The second electrode and magnetic pole 24 is provided by the upper annular face 96 of the cup-shaped, upwardly open receptacle 73. Consequently, the operational, annular gap 26 is formed between the outward lateral and upper annular surfaces of said washer 80 and said upper face 96 of said cup-shaped receptacle 73, together with the lateral inside surface of said cup-shaped receptacle 73 adjacent to the inner periphery of said annular upper face 96.

Figure 3:
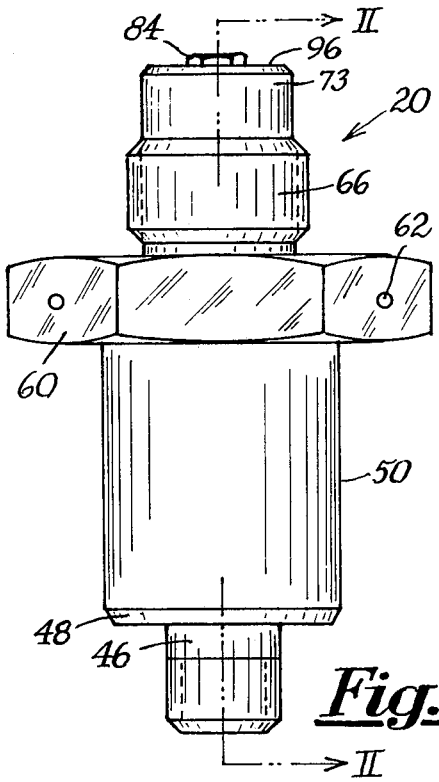

The elements which are visible from a completely assembled device 20 can readily be recognized in FIG. 3.

The principle expounded in the foregoing for a wear particle detector utilizing one capacitor and its specific discharge impulse current for the destruction of wear fuzz particles of correlated dimensions can be expanded within the frame of this invention to a system capable of differentiating — and destroying — particles ranging from a given small to a given large wear fuzz size with any desired, discrete, intermediate operating steps. A possible application of this teaching is depicted in the electric circuit diagram of FIG. 4, employing, substantially, if not wholly, the identical basic component part types as the device described for the schematic, FIG. 1.

Figure 4:
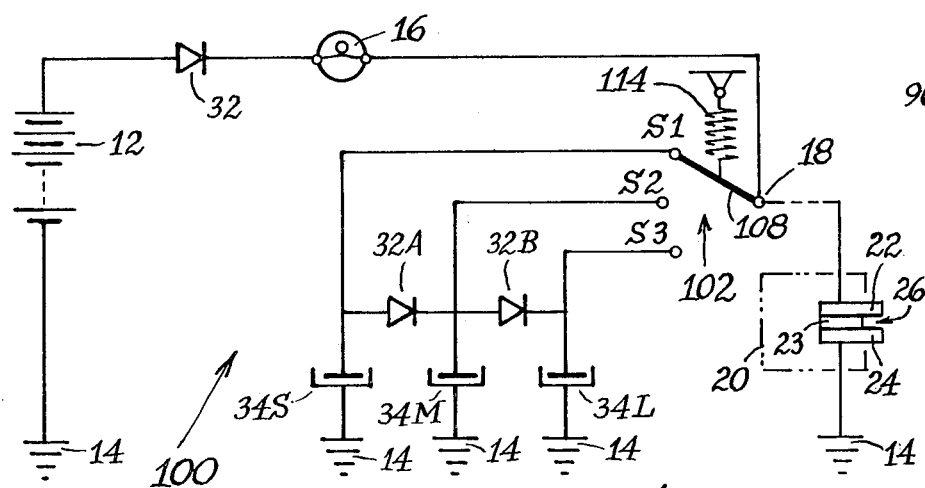

The aforementioned schematic 100, as shown in FIG. 4, indicates a power source 12 and a bulb 16 connected in series with each other to return 14 and to terminal 18 of said wear particle detector 20, respectively, in the same manner as shown and described for the arrangement in FIG. 1.

The following component parts as connected with each other as presented in the schematic 100: The electrodes 22 and 24, the gap 26 between them and the permanent magnet 23 are identical with those in FIG. 1. The electrode 24 is connected to return 14, whereas the electrode 22 is connected to the device terminal 18. In place of a former single capacitor 34, a discrete number of, for example, three capacitors, namely, 34S, 34M and 34L are provided.

It should be noted that the capacitances of the, in this example, three capacitors vary from each other as follows: The capacitor 34S has the smallest of the three capacitances, capacitor 34L the largest and capacitor 34M a capacitance of a value between said smallest and said largest capacitance, whereby the absolute values of said capacitances depend on their particular application without affecting the principle of the herein described configuration.

The, in these cases, negative pole of each, for example, polarized capacitor 34S, 34M and 34L is connected to return 14. In this case, two diodes 32A and 32B are provided; diode 32A allows for the flow of current from the positive pole of capacitor 34S to capacitor 34M, diode 32B from the positive pole of capacitor 34M to capacitor 34L, but not in the respective reverse directions. The diode 32 is arranged in the line and in series with said bulb 16. It should be noted that the diodes are oriented so as to permit the flow of current from the positive pole, the line, of the power source 12 to return 14, but to block it in the opposite direction.

A, for example, three-position, break-before-make switch 102 is provided for the selective operation of said capacitors. The wiper arm 108 of said switch is mounted on, but electrically insulated from, the switch actuator (not shown). The pivot of said wiper arm 108 is connected to the terminal 18 of said wear particle detector 20. In this case, the three stationary switch contacts S1, S2 and S3 are connected with the positive poles of said capacitors 34S, 34M and 34L, respectively. A mechanical expansion spring 114 is fixedly mounted at one of its two ends and on the wiper arm 108 of said switch 102 with its other end, thusly biasing said wiper arm 108 toward its return to the "standby" position at contact S1, should the manual actuation of said switch 102 be absent and cease, selectively.

The operation of the foregoing system is as follows: In the, say, "standby" position of said wiper arm 108 on said switch contact S1, as shown in FIG. 4, the three capacitors 34S, 34M and 34L become fully charged and the electrodes 22 and 24, together with the gap 26 between them, are prepared for the closing of the circuit by a wear particle arriving at the wear particle detector 20. When a wear particle becomes lodged across said gap 26 and securely arrested by said permanent magnet 23 and thereby connects the electrode 22 with the electrode 24, it causes said bulb 16 to light and to serve as a warning signal, unless said wear particle is exceedingly small in cross section and becomes destroyed through the discharge impulse current of said capacitor 34S. Should, however, said wear particle not become destroyed through the discharge impulse current of said capacitor 34S, as indicated through the continued lighting of said bulb 16, an operator will actuate said switch 102 successively to the switch contact positions S2 and S3, thereby causing capacitors of increasingly larger capacitances to discharge through said wear particle in an attempt to destroy it, provided it has a cross-section receptive to such destructive discharge currents.

It is obvious that the operator will refrain from any switch actuation beyond that switch position at which a wear particle destruction occurred. It is also self-evident that remedial actions will be taken if the warning light of said bulb 16 remains lit after all switch positions have been consummated and all capacitor charges exhausted.

It should be noted that in the circuit and component parts configuration depicted in FIG. 4, each said capacitor 34S, 34M and 34L remains connected with the line while selected to deliver its charge through the to-be-destroyed particle and that, likewise, each successive, not yet selected capacitor remains connected with the line. In this fashion, several repetitive particle destructions and automatic capacitor recharge cycles are available for each individual switch position S1, S2 and S3, in addition to the manual selection of, in this example, three specific discharges of increasing intensities. It should further be noted that in the arrangement of FIG. 4 all component parts of the wear particle detection system, except the electrodes 22 and 24 and the operational gap 26, are positioned outside of the enclosure of said wear particle detector 20 (as indicated in phantom lines). Whereas this configuration is not intended to be mandatory and otherwise restricted to the teachings shown in FIG. 4, it may be advantageous for specific new applications and for modifications to existing circuits.

Figure 5:
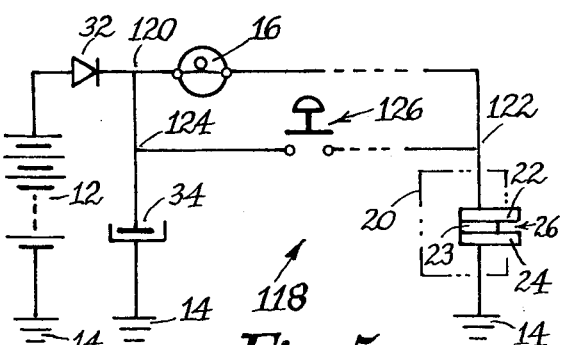

A further embodiment within the spirit of this invention is presented in FIG. 5, having several previously described elements in the circuit arrangement 118. The power source 12 is connected to return 14 at its negative pole, while its positive pole is connected with the positive pole of the blocking diode 32; the negative pole of said diode 32 is wired to the junction 120 and thence to one terminal of the bulb 16; the other terminal of said bulb 16 is connected with the junction 122 and thence with the electrode 22; the electrode 24 is connected to return 14. A branch circuit originates at junction 120, passing through junction 124 to the positive pole of the capacitor 34; the negative pole of said capacitor 34 is connected to return 14. A normally open, for example, double break, push button switch 126 is connected to junction 124 with one of its terminals and to junction 122 with its other terminal.

The operation of this embodiment in accordance with the circuit schematic 118 of FIG. 5 is as follows: With the circuit connected to the power source 12, the capacitor 34 becomes and remains charged, and the electrodes 22 and 24 are prepared to close the circuit for the bulb 16 if at least one wear particle (not shown) has become lodged across the gap 26 formed by said electrodes 22 and 24, causing said bulb 16 to light, thereby indicating the presence of a wear particle. Alerted by the lit bulb 16, an operator actuates and closes said switch 126, thereby releasing the charge of said capacitor 34 through the wear particle lodged across said gap 26. Should the wear particle have a sufficiently small cross-sectional area, it will be destroyed and the bulb 16 will extinguish. In this case, the capacitor 34 will become recharged to be ready for the next such operation. Should, however, the wear particle have a cross-sectional area too large with respect to the destructive capability of the capacitor's discharge current, the bulb 16 will remain lit and indicate the need for remedial actions of other kinds.

It becomes apparent that the device configuration of FIG. 5 will be the preferred arrangement for those applications where failure modes are expected which generate large quantities of small wear particles. If the warning light, namely, the bulb 16 comes on frequently, the operator, for example, an aircraft pilot, realizes that such a failure condition is developing.

In the case of the circuit components corresponding to FIG. 5, they may, likewise, be located exteriorly with respect to the enclosure of said wear particle detector 20 (shown in phantom lines).

It becomes apparent that each of the foregoing embodiments may be modified to suit particular operational requirements other than shown herein and altered accordingly without departing from the spirit of this invention.

What is claimed is:

1. A wear particle detector for the attraction, collection, automatic destruction and indication, selectively, of wear particles present in hydraulic systems and adapted for connection with an electric power source, comprising:

a pair of electrodes of electrically and magnetically conductive material spaced apart so as to form an operational gap of predetermined dimensions and thereby constituting a discontinuity of an energized electric indicating circuit adapted to attract and to collect wear particles, a means to provide a magnetic field between said electrodes, and at least one capacitor of a predetermined capacitance connected in parallel with said operational gap so as to cause at least one release of the charge of said capacitor through at least one wear particle attracted and collected by said electrodes across said gap and the then closed electric circuit, the destruction of said at least one wear particle, followed by an automatic recharging of said at least one capacitor, and an alarm means, said means being activated should said at least one wear particle not have become destroyed.

2. A wear particle detector as defined in claim 1, wherein means are provided for the suppression of transients and discharge effects, respectively, from said at least one capacitor to the remaining portions of the wear particle detector which further includes a power source and means for transmitting power from said power source to said at least one capacitor and to said electrodes.

3. A wear particle detector as defined in claim 2, wherein
means are provided for the gradual discharging of said capacitor upon the disconnection of a said wear particle detector from the line of said power source.

4. A wear particle detector as defined in claim 3, wherein
said capacitor,
said means for the suppression of transients and discharge effects and
said means for the gradual discharging of each said capacitor upon removal from the line of said power source
are mounted within the enclosure of said wear particle detector.

5. A wear particle detector as defined in claim 3, wherein
said capacitor,
said means for the suppression of transients and discharge effects and
said means for the gradual discharging of each said capacitor upon the removal of said wear particle detector from the line of said power source
are located exteriorly with respect to said wear particle detector enclosure
and are adapted for electric connection with said at least one set of electrodes which are mounted to said wear particle detector enclosure.

6. A wear particle detector as defined in claim 5, wherein
a plurality of said capacitors is provided having predetermined capacitances varying in predetermined discrete increments from each other and ranging from a specific small to a specific large capacitance, and
means for the sequencing of selective connections for said at least one set of electrodes and each said capacitor of said plurality of capacitors from the line of said power source, to each said capacitor in the order from that capacitor having the smallest capacitance to that said capacitor having the largest capacitance.

7. A wear particle detector as defined in claim 1 wherein
each said electrode is made of a ferrous and electrically conductive material and
a permanent magnet is mounted between each said set of electrodes.

8. A wear particle detector as defined in claim 1, wherein
an electrically nonconductive insulating means is provided between each said permanent magnet and at least one said electrode of each said set of electrodes.

9. A wear particle detector as defined in claim 1 wherein
each said electrode is made of a permanently magnetized ferrous and electrically conductive material and
positioned with respect to each other so as to provide opposite magnetic polarities at any two coacting ends of each said set of said electrodes.

10. A wear particle detector for selectively attracting, detecting and destroying wear particles suspended in hydraulic systems, comprising:
a substantially cylindrical enclosure having a substantially cylindrical, axial, externally threaded extension on its top and a flange formed on it laterally,
a first, upwardly open, axial, cylindrical port formed in said extension concentrically with the axis of said wear particle detector,
a second, downwardly open, axial, cylindrical port formed in said enclosure concentrically with the axis of said wear particle detector,
an axial, cylindrical hole formed in said enclosure concentrically with the axis of said wear particle detector, establishing communicating between said first and said second port,
a third, downwardly open, axial, cylindrical port formed in said enclosure concentrically with the axis of said wear particle detector, having a diameter larger than the diameter of said second port so as to provide an annular offset shoulder between said second and said third port,
a cup-shaped, upwardly open receptacle, having a cylindrical hole concentric with the axis of said receptacle and said wear particle detector formed in its bottom and said extension,
an annular, permanent magnet of ceramic and electrically nonconductive material positioned within said receptacle,
a washer of magnetically and electrically conductive material positioned concentrically with the axis of said wear particle detector,
a first annular spacer of electrically nonconductive material positioned underneath said cylindrical extension of said cup-shaped receptacle and within said first port,
an annular seal of electrically nonconductive material positioned underneath said first annular spacer and within said first port,
a second annular spacer of electrically nonconductive material positioned underneath said annular seal and within said first port,
a washer of electrically nonconductive material mounted concentrically with the axis of said device and the top of said second cylindrical port,
a wire terminal, having a ring tongue and a barrel, mounted with said ring tongue underneath said washer,
a screw bolt, having a head at its top and externally threaded portion at its bottom, inserted through and extending downwardly beyond said electrically and magnetically conductive washer, said permanent, annular magnet, said cylindrical hole formed in said cup-shaped receptacle and its cylindrical extension, said first annular spacer, said annular seal, said second annular spacer, said cylindrical hole formed between said first and said second port, said electrically nonconductive washer and said ring tongue of said wire terminal,
a binding nut mounted on said extending threaded portion of said screw bolt so as to contain said parts,
a circuit board, having a cylindrical shape, positioned concentrically with the axis of said wear particle detector at the top of said third port and abutting against said shoulder formed between said second and said third port,
a spacer, having the shape of a hollow cylinder positioned concentrically with the axis of said wear particle detector inside of and contiguous with the lateral inside surface of said third port, and abutting with its upper annular face against the lower surface of said circuit board, a face plate, having a cylindrical shape and positioned concentrically with the axis of said wear particle detector and having a cylindrical hole formed therein concentrically with the axis of said wear particle detector, abutting with its upper surface against the lower annular face of said spacer, an electric connector receptacle, having an external thread formed on its lower portion and at least one terminal pin, said electric connector receptacle mounted in said cylindrical hole formed in said face plate, said face plate equipped with said electric connector receptacle mounted on and at the bottom of said third port, a diode, having two leads mounted on the upper surface of said circuit board, one said lead being connected with said at least one terminal pin of said electric connector receptacle, the other lead being connected with said barrel of said wire terminal, a resistor, having two leads, mounted on the upper surface of said circuit board, one said lead being connected with said barrel of said wire terminal, the other lead being connected with a second terminal pin of said electric connector receptacle and said enclosure of said wear particle detector, selectively, a capacitor, having two leads, mounted on the lower surface of said circuit board, one said lead being connected with said barrel of said wire terminal, the other lead being connected with a said second terminal pin of said electric connector receptacle and said enclosure of said wear particle detector, selectively, said wear particle detector adapted for the connection of said at least one terminal pin of said electric connector receptacle with an electric circuit supplying the power for the detection and destruction of wear particles.

11. A wear particle detector as defined in claim 10, wherein a sheath of an electrically nonconductive material being impervious to the incident hydraulic fluid is mounted within said cup-shaped receptacle so as to isolate electrically said electrically and magnetically conductive washer from said cup-shaped receptacle.

* * * * *